(12) United States Patent
Fowler et al.

(10) Patent No.: US 7,385,215 B2
(45) Date of Patent: Jun. 10, 2008

(54) SENSOR ELEMENTS FOR SUPERCAVITATING VEHICLES

(75) Inventors: Kim R. Fowler, Windsor Mill, MD (US); Leo R. Gauthier, Jr., Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 59 days.

(21) Appl. No.: 11/478,984

(22) Filed: Jun. 30, 2006

(65) Prior Publication Data

US 2007/0002475 A1  Jan. 4, 2007

Related U.S. Application Data

(60) Provisional application No. 60/695,337, filed on Jun. 30, 2005.

(51) Int. Cl.
*G01N 21/86* (2006.01)
*G01V 8/00* (2006.01)

(52) U.S. Cl. .............................. 250/559.4; 250/559.19; 250/559.2

(58) Field of Classification Search ............... 250/559.4, 250/559.19, 559.2, 227.25
See application file for complete search history.

(56) References Cited

U.S. PATENT DOCUMENTS 6,084,519 A * 7/2000 Coulling et al. ............. 340/602

6,957,579 B1  10/2005 Antonelli et al.
7,123,544 B1 * 10/2006 Kuklinski ..................... 367/89

FOREIGN PATENT DOCUMENTS

JP          359192921 A   * 11/1984

OTHER PUBLICATIONS

R. Kamada, "Trajectory Optimization Strategies for Supercavitating Vehicles" paper School of Aerospace Engineering, Georgia Institute of Technology, Nov. 2005.

* cited by examiner

*Primary Examiner*—Georgia Y. Epps
*Assistant Examiner*—Francis M Legasse, Jr.
(74) *Attorney, Agent, or Firm*—Francis A. Cooch

(57) ABSTRACT

Sensing elements that quickly and accurately determine if a liquid or gas is present around the sensing elements are disclosed. These sensing elements find particular application in identifying the location of the cavity wall in which a supercavitating vehicle is operating, relative to the vehicle. In certain embodiments signal emitting elements carried on the vehicle emit signals towards the presumed position of the cavity wall, and sensing elements carried on the vehicle receive the emitted signals after they are reflected off of the cavity wall. The sensing elements identify the location where the reflected signal is received, and based on this identified location, the location of the cavity wall is determined. In alternative embodiments, sensing elements are positioned along fins extending outward with respect to the hull of the vehicle, and the sensors sense the presence of liquid or gas.

20 Claims, 5 Drawing Sheets

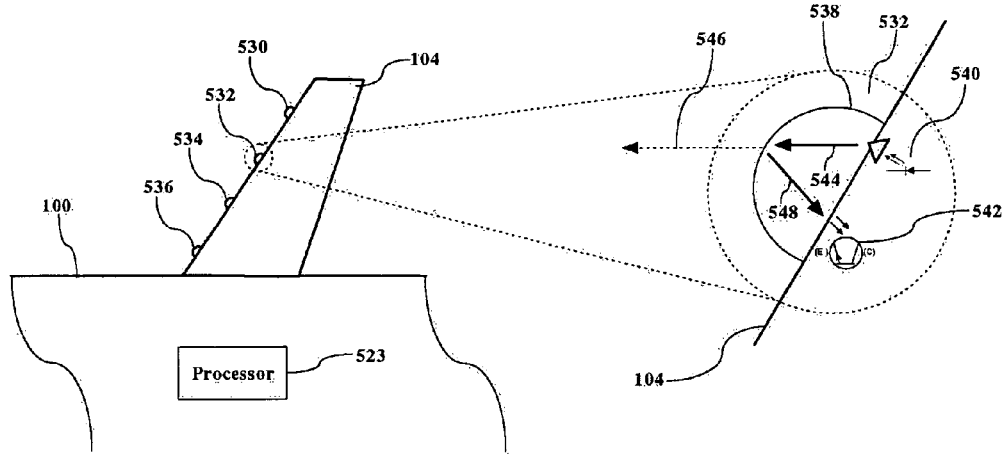
Figure 5a
Figure 5b
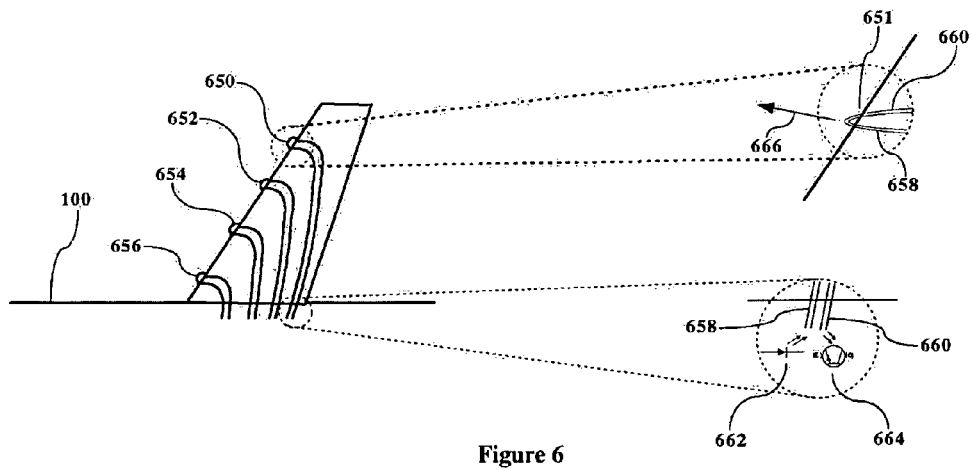
Figure 6

SENSOR ELEMENTS FOR SUPERCAVITATING VEHICLES

CROSS-REFERENCE TO RELATED APPLICATIONS

This application claims the benefit of prior filed co-pending U.S. application No. 60/695,337, filed on Jun. 30, 2005, the content of which is incorporated fully herein by reference.

BACKGROUND OF THE INVENTION

1. Field of the Invention

This invention relates to methods and systems for sensing the presence or absence of liquid or gas around a sensor and, more particularly, for sensing and tracking the location of the wall of the cavity formed about a supercavitating vehicle and, even more particularly, to the sensing and identifying the location of the cavity wall relative to an underwater supercavitating vehicle without measuring the time-of-flight of an optical or RF signal.

2. Description of the Related Art

The U.S. Navy has funded long-running research programs for controlling supercavitating projectiles and vessels, referred to herein generically as supercavitating vehicles. Some of this work extends back to the 1940's and 1950's. The non-linear and high-speed nature of supercavitation makes control of supercavitating projectiles and vessels difficult.

Operating and controlling a supercavitating vehicle in an optimal manner involves limiting friction exerting drag on the vehicle. As is well known, a supercavitating vehicle operates within a cavity formed around the vehicle and contact between the supercavitational vehicle and the wall of the cavity increases the friction and thus the drag exerted on the vehicle. Thus, it is important to be able to extract and measure where the wall of the cavity is located, so that the vehicle can be operated in a manner that minimizes contact between the vehicle and the cavity wall. Stable guidance of the vehicle is critically dependent upon maintenance of the cavity so as to limit the friction exerted on the vehicle, and this guidance is dependent upon having quick and accurate information about the location of the cavity wall relative to the vehicle at all times. Thus, it is desirable to have a method for sensing and tracking the location of the cavity wall quickly and accurately.

SUMMARY OF THE INVENTION

The present invention pertains to sensing elements that quickly and accurately determine if a first changing media of a first index of refraction or a second changing media of a second index of refraction is present around the sensing elements. These sensing elements find particular application in identifying the location of the cavity wall in which a supercavitating vehicle is operating, relative to the vehicle, particularly where the first media is a liquid and the second media is a gas. In certain embodiments signal emitting elements carried on the vehicle emit signals towards the presumed position of the cavity wall, and sensing elements carried on the vehicle receive the emitted signals after they are reflected off of the cavity wall. The sensing elements identify the location where the reflected signal is received, and based on this identified location, the location of the cavity wall is determined. In alternative embodiments, sensing elements are positioned along fins extending outward with respect to the hull of the vehicle, and the sensors sense the presence of liquid or gas. Sensors sensing gas identify portions of the fin that are located within the cavity, and sensors sensing liquid identify portions that are located beyond the cavity wall. This enables quick and accurate location of the location of the cavity wall.

BRIEF DESCRIPTION OF THE DRAWINGS

FIG. 5 illustrates an alternative embodiment for sensing the location of a cavity wall relative to the vehicle;

FIG. 6 illustrates an alternative embodiment for sensing the presence or absence of water along the fin.

DETAILED DESCRIPTION

The present invention is a method and system for sensing the presence of changing media having differing indices of refraction, e.g., gas or liquid, around a sensor, and in a preferred embodiment, this information is used for monitoring the location of the cavity wall surrounding a supercavitational vehicle, relative to that vehicle. The examples illustrated herein all pertain to underwater vessels where the vessel is operating in water and the cavity is formed by the absence of water created by a cavitation. However, it is understood that the sensors of the present invention can be used in any environment where the sensor is in contact with media having differing indices of refraction; air and water are used for the purpose of example. It is contemplated that a shock boundary between two gaseous media (as would be found in a supercavitating missile operating in the earth's atmosphere) could be detected using the principles of the present invention.

Figure 1:
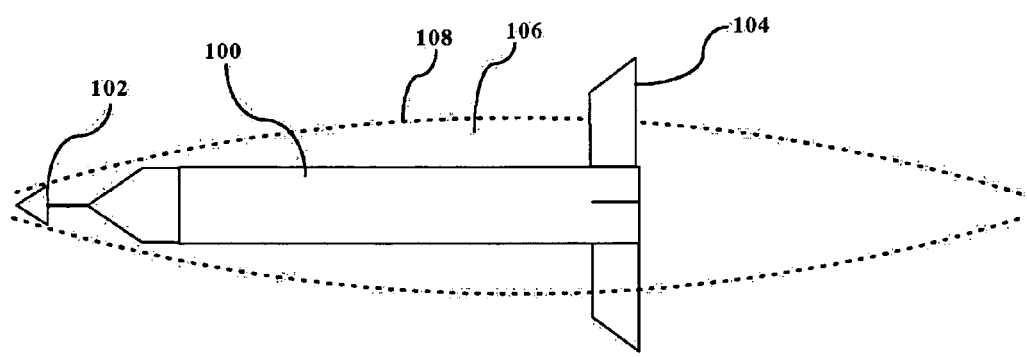
FIG. 1 illustrates the known concept of creating a cavity around a supercavitational vehicle.

FIG. 1 illustrates the known concept of creating a cavity around a supercavitational vehicle. Referring to FIG. 1, a vehicle 100 (e.g., a torpedo traveling through water) has a cavitator 102 attached at the front of the vehicle 100. In a well known manner, cavitator 102 creates an air cavity 106 surrounding the vehicle 100. A cavity wall 108 defines the border between the air cavity 106 and the fluid in which the vehicle 100 is traveling. Fins 104 extend away from vehicle 100 in a well known manner and are utilized for stabilizing and controlling the vehicle 100. It is understood that the vehicle illustrated in FIG. 1 is schematic in nature and is not to scale, but is instead utilized to identify the various parts of the structure and their relationship to the air cavity 106.

Figure 2:
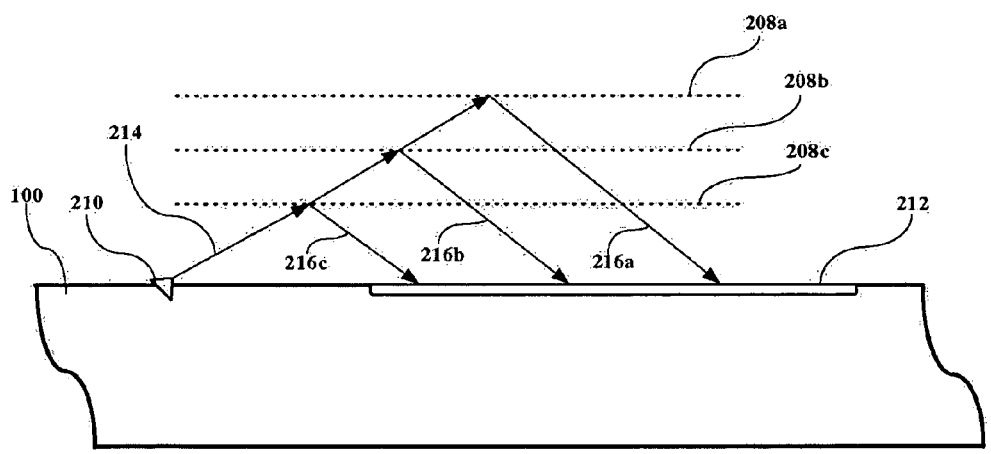
FIG. 2 illustrates a first embodiment of the present invention.

FIG. 2 illustrates a first embodiment of the present invention. A light source 210 (e.g., a laser, LED, or the like) is configured into the hull of vehicle 100 and directs a light beam at a predetermined angle away from the vehicle 100. In a preferred embodiment the light source 210 comprises a laser, because this embodiment makes use of the Snell's law of reflection, i.e., that the angle of incidence of a light beam is equal to the angle of reflection of the light beam. As such, since a laser can be more specifically directed to a point of reflection, a laser will result in a more accurate result. An LED, while functional for this purpose, has a more multi-directional emission.

A series of light-sensitive receivers illustrated collectively as sensing element 212 of FIG. 2 are positioned along the hull of vehicle 100 such that light reflecting off of cavity wall 108 will be received by one or more of the light sensors in sensing element 212. The exact positioning of sensing element 212 can be determined in a known manner based upon the angle at which the light source 210 emits its light and the estimated maximum and minimum distances between the vehicle 100 and the cavity wall 108. These maximum and minimum distances can be determined based upon the operational specifications of vehicle 100. Further, the distance along the hull between the light source 210 and each of the light-sensitive receivers comprising sensing element 212 are known and these values are stored in a processor (not shown) on board vehicle 100, which processor is configured to receive and process data signals from the light-sensitive receivers.

As shown in FIG. 2, three different cavity wall positions, cavity wall position 208*a*, cavity wall position 208*b*, and cavity wall position 208*c*, are illustrated by dotted lines. At any given moment there will only be a single cavity wall; however, since vehicle 100 is traveling in fluid, the position of the cavity wall relative to the vehicle 100 will fluctuate, and this fluctuation is illustrated by the three cavity wall positions 208*a*, 208*b*, and 208*c*.

The basic operation of the configuration shown in FIG. 2 is now described. The light source 210 emits a light beam 214. In a well known manner, upon the light beam 214 striking the cavity wall, a significant portion of the light beam 214 is reflected back towards the vehicle 100. For example, as shown in FIG. 2, if the cavity wall is located at position 208*a*, light source 214 will travel up to the cavity wall at position 208*a* and then reflect back towards sensing element 212 as reflected beam 216*a*. If the cavity wall is closer to the vehicle at position 208*b*, the light beam 214 will be reflected back towards sensing element 212 as reflected beam 216*b*. Finally, if the cavity wall is at location 208*c*, the light beam 214 is reflected back towards sensing element 212 as reflected beam 216*c*.

As can be seen from FIG. 2, the location of the cavity wall will determine where on sensing element 212 the light beam is reflected. By determining where along sensing element 212 the light beam is received (i.e., identifying which of the light-sensitive receivers receives the reflected light beam), the processor can be used to calculate the approximate perpendicular distance between the vehicle 100 and the cavity wall, referred to herein as the "standoff distance". Specifically, the standoff distance SD can be calculated using the formula $SD=(X/2)*\tan(\theta)$, where X is the distance along the hull from the light source 210 to the light-sensitive receiver receiving the reflected beam, and theta is the angle between the light beam 214 and the hull. Since each light-sensitive receiver will have a unique value of X (distance along the hull from light source 210 to the light-sensitive receiver), the value of SD can be calculated easily and quickly.

Figure 3:
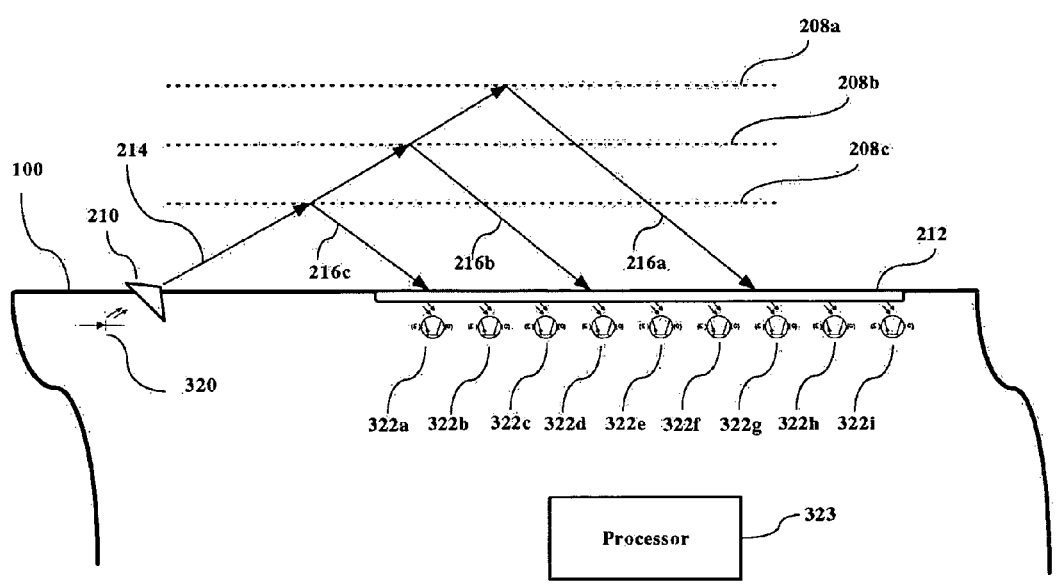
FIG. 3 illustrates a configuration of the embodiment discussed in FIG. 2 in which more detail is provided regarding the sensing element.

FIG. 3 illustrates a configuration of the embodiment discussed in FIG. 2 in which more detail is provided regarding the sensing element 212. Referring to FIG. 3, a laser 320 is utilized as the light source and projects light beam 214 out away from the vehicle as described previously. Sensing element 212 comprises a plurality of photo-resistive diodes 322*a*-322*i*. Each of the photo-resistive diodes 322*a*-322*i* is coupled to a processing element 323 (connections omitted for simplicity), the function of which is described in more detail below. Thus, whichever of the photo-resistive diodes 322*a*-322*i* receives the reflected light beam from the cavity wall will sense a threshold level of received light that is significantly higher than those received by the remaining photo-resistive diodes. Accordingly, with knowledge of the angle at which light beam 214 leaves vehicle 100, relative to the vehicle, and knowledge of which of the photo-resistive diodes is currently receiving the reflected beam, a simple calculation can be made to determine the standoff distance between the cavity wall and vehicle 100. It is understood that although photo-resistive diodes are illustrated herein, numerous alternatives for the light-sensitive receiver will be apparent to a designer of ordinary skill in the art and such alternatives are covered by the appended claims.

Figure 4:
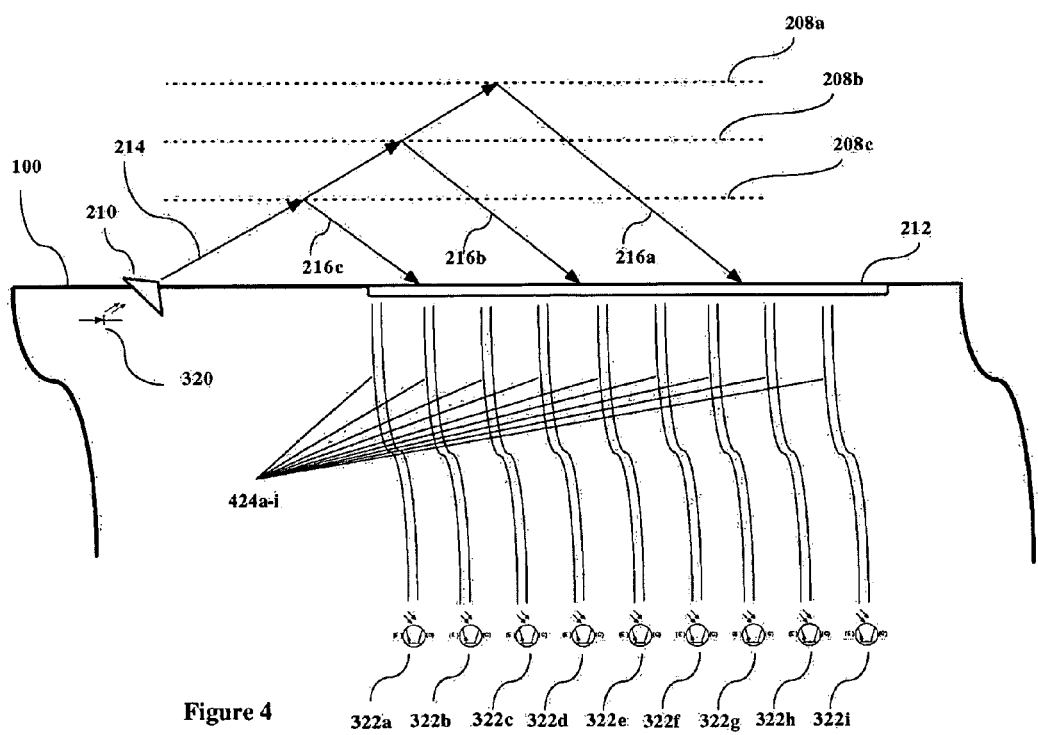
FIG. 4 illustrates an alternative embodiment, whereby a fiber optic bundle conveys the light received after reflection off of the cavity wall to the bank of photo-resistive diodes.

FIG. 4 illustrates an alternative embodiment, whereby a fiber optic bundle comprising, in this example, optical fibers 424*a*-424*i*, convey the light received after reflection off of the cavity wall to the bank of photo-resistive diodes 322*a*-322*i*. The operation is otherwise identical to that of FIG. 3. With respect to FIGS. 3 and 4, it will be understood that nine photo-resistive diodes and/or photo-resistive diode/optical fiber pairs are shown for the purpose of example and that these numbers may be increased or decreased depending upon the needs of a particular designer.

FIG. 5 illustrates an alternative embodiment for sensing the location of a cavity wall relative to the vehicle 100. In this embodiment, sensors referred to herein as "dome sensors" are situated along at least one of the fins 104 projecting outward from vehicle 100. In the illustration of FIG. 5*a*, four such dome sensors 530-536 are illustrated, with details of the dome sensors 530-536 being illustrated in FIG. 5*b*. It is noted that, although not shown, electrical connections are utilized to connect the dome sensors to the processing circuitry 523 to enable transmission of the output of each dome sensor to the processing circuitry so that the presence or lack thereof of a liquid or a gas in contact with the dome sensors can be ascertained. Further, although there are four dome sensors shown, it is understood that in most instances there would likely be many more dome sensors to increase the resolution of the sensing of the location of the cavity wall.

Referring to FIG. 5*b*, each dome sensor includes a light source 540 (e.g., an LED, laser, etc.) and a light sensitive receiver 542 (e.g., photo diode, photo transistor, etc.). A dome 538, made of glass, plastic, ceramic, or any other material that will allow light to pass therethrough, extends outward from the fin 104, such that the dome 538 contacts any gas or liquid in contact with the portion of the fin 104 on which the dome sensor is situated. If desired, optical fibers can be situated between the light source 540 and the light receiving element 542 to direct the light to and from the dome 538. The dome 538 is a fixed media that forms a reflective/refractive interface with a changeable media (e.g., a first changeable media such as water, a second changeable media such as gas, etc.).

The operation of the dome sensor is as follows. Light source 540 emits a light beam 544. When the dome 538 is in contact with water or other liquid a large portion of the light beam 544 refracts out into the liquid (illustrated by dotted line 546) and thus is not reflected back to the light sensing element 542. However, in situations where there is no liquid in contact with the dome 538, the light beam 544 reflects off the inside of the dome 538 and is received at light-sensitive receiver 542 (illustrated by line 548). Since there will be significantly more light received at light-sensitive receiver 542 when there is no liquid present outside of the dome 538, the processing circuitry is able to identify when a liquid is present (sensing of a level of light below a predetermined threshold), and when a liquid is not present (sensing of a level of light at or above a predetermined threshold). Accordingly, an indication of a liquid being present indicates that the particular dome sensor indicating the presence of the liquid is beyond the cavity wall (i.e., it is in the liquid). However, dome sensors that are within the cavity will sense the presence of air (or the lack of water), indicating they are within the cavity. Therefore, it is possible to identify approximately where along the fin 104 the border between the cavity and the water exists, thereby identifying the approximate location of the cavity wall.

FIG. 6 illustrates an alternative embodiment for sensing the presence or absence of water along the fin 104. Referring to FIG. 6, a series of optical fibers 650, 652, 654, and 656 are shown. Each optical fiber comprises a loop of fiber which originates within the vehicle 100, travels along fin 104 to a particular location along the edge of fin 104, has a bent portion extending beyond, or flush with, fin 104 and then returns back to vehicle 100 (in FIG. 6 the bent portion is shown as extending beyond the fin; the bent portion can instead be flush with the fin so as not to protrude out from the fin). This configuration defines multiple paths from the vehicle to an outer edge of fin 104 and back to the vehicle. In the example of FIG. 6 there are four such optical fiber elements shown; however, it is understood that in most configurations there will be many more such elements and the more elements there are, the better the resolution of the sensing of the location of the cavity wall.

Shown within the dotted line circles in FIG. 6 are exploded views of the exposed bent element 651 of fiber 650 and the ends 658 and 660 of fiber 650. A light source 662 is situated at the outbound end 658 of fiber 650 and inputs light thereto in a well known manner. The light travels along outbound portion 658 until it reaches the bent element 651, which is exposed outside of, or flush with, the fin 104 such that it is in contact with any liquid or gas that is in contact with fin 104 at that point. The bent element 651 forms a reflective/refractive interface with changeable media (e.g., water, air, etc.) coming in contact therewith. If a liquid is in contact with the bent element 651, light traveling along outbound path 658 will refract out into the water and thus minimize the amount of light that continues along fiber 650 down the inbound path 660. However, in the absence of water, light traveling along outbound path 658 will continue around the bent element 651 and be returned along inbound path 660 to a light-sensitive receiver element 664. The sensor of FIG. 6 utilizes the known property of optical fibers that light can leak from bends in the fiber. The boundary between two transparent media having different indices of refraction (in this example, there will be either a fiber/air interface or a fiber/liquid interface) will refract and reflect light differently, depending on the particular types of media. The measurable quantity of light returning on fiber is modulated by the change in the external medium in an identifiable way, allowing the type of media to be discerned as described above with respect to the dome sensor.

Figure 7:
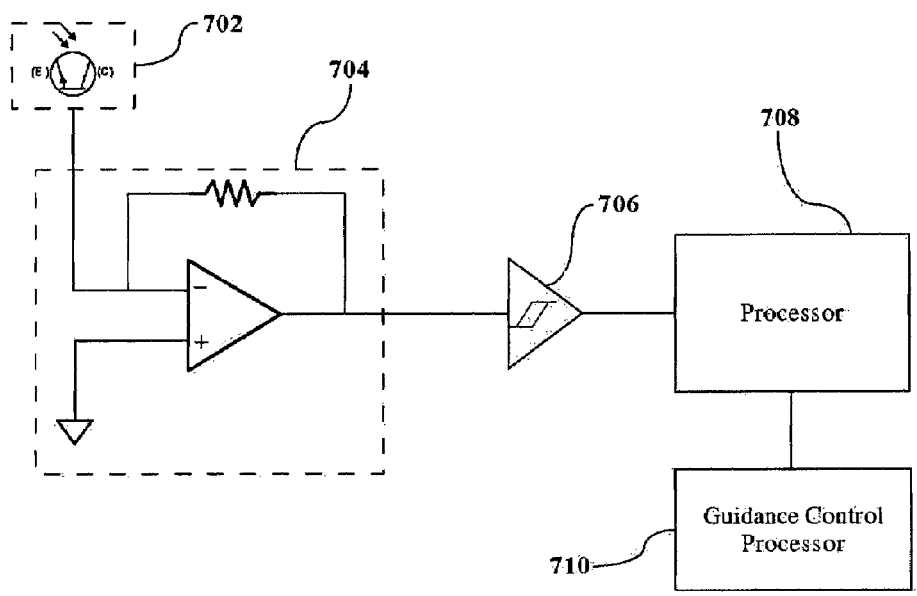
FIG. 7 illustrates an example of a typical processing circuit that can receive the outputs from the light-sensitive receivers and utilize this information to determine the cavity wall location and, if desired, control guidance of the vehicle.

FIG. 7 illustrates an example of a typical processing circuit that can receive the outputs from the photodiodes and utilize this information to determine the cavity wall location and, if desired, control the guidance of the supercavitational vehicle. It is understood that this circuit is presented for the purpose of example only and that there are multiple other configurations that can be utilized to perform this function.

The output of each light-sensitive element (702 in FIG. 7 is representative of each photodiode or other light-sensing element) is input to a wideband photodiode amplifier 704 which converts the photodiode current into an amplified voltage. Threshold device 706 (e.g., a comparator) compares the voltage output from the wideband photodiode amplifiers to predetermined voltage references set for each sensor. A logic 1 is output from the threshold device 706 only if its threshold is exceeded. Accordingly, until the light received at a particular light-sensing element 702 is of a level which will output a current that, when amplified by the wideband photodiode amplifier 704 exceeds the threshold level, there will be a logic 0 output from threshold device 706. Therefore, if water is present, a logic 0 will be output, and if air water is present, a logic 1 level will be output.

The output of each threshold device 706 is input to processor 708. Processor 708 is configured to identify which light-sensitive receivers are sensing the presence of water and which are sensing the presence of gas. Data regarding the location of each sensor is stored in processor 708, and thus a determination can be made as to the location of the cavity wall. As the cavity wall moves, different light-sensitive receivers receive the reflected light, and hence the correspondence between the photo detection and cavity wall location changes accordingly.

The time to complete processing and make steering adjustments in a supercavitating vehicle varies from 100 µsec for speeds of 20 m/s to less than 2 µsec for speeds of 1000 m/s. These calculations assume a maximum displacement of 2 mm before correction occurs. The sensors described herein can have response times as low as 1 µsec or less. Each of the sensors give a robust indication of the proximity of the cavity wall, in a very short period of time.

A control system utilizing the sensors of the present invention can be a guidance control processor 710 which receives the data from processor 708 that discriminates between the various media around each sensor and thus can determine the location of the cavity wall relative to the vehicle, and guidance control processor 710 can then actuate the control fins on the supercavitating projectile or vessel. This configuration can use a classical approach to control system design, for example, the system described in Dzielski and Kurdila ("A Benchmark Control, Problem for Supercavitating Vehicles and an Initial Investigation of Solutions," Pennsylvania State University and University of Florida). Alternatively, the control system could take a much more neural network approach, so that the guidance control processor is really only a collection of "neural synapses" such as an animal nervous system ganglian or simple insect brain, as described in Zbikowski ("Sensor-Rich Feedback Control," *IEEE Instrumentation and Measurement Magazine*, Vol. 7, No. 3, pp. 19-26). This neural network type of control system has been described by Zbikowski as a "sensor-rich system" and not "actuator-rich", since as many sensors as desired can be utilized to monitor the proximity of the supercavitating cavity wall without increasing the number of actuators or control fins. The advantage of this type of control system is that it is conceptually simple and relatively easy to implement in hardware and software.

While there has been described herein the principles of the invention, it is to be understood by those skilled in the art that this description is made only by way of example and not as a limitation to the scope of the invention. Accordingly, it is intended by the appended claims, to cover all modifications of the invention which fall within the true spirit and scope of the invention.

The invention claimed is:

1. A sensor for sensing the presence of media in contact with the sensor, comprising:
    a light source emitting an optical signal;
    a light sensitive receiver positioned to detect a reflection of said optical signal, said light sensitive receiver generating a reflection signal corresponding to an index of refraction of said media;
    a reflective/refractive interface positioned between said light source and said media; and
    a processing circuit coupled to said light sensitive receiver, said processing circuit configured to receive said reflection signal and compare said reflection signal with a predetermined threshold value;

wherein if said received reflection signal meets or exceeds said threshold value, a determination is made that a first media is in contact with said reflective/refractive interface, and wherein if said received reflection signal is less than said threshold value, a determination is made that said first media is not in contact with said reflective/refractive interface; and wherein said sensor is incorporated in a supercavitational vessel to sense a distance between said supercavitational vessel and a cavity wall formed by operation of said supercavitational vessel.

2. The sensor of claim 1, said sensor sensing the presence of said first or a second media, said first and second media having differing indices of refraction, wherein:

said light sensitive receiver generates a first reflection signal corresponding to an index of refraction of said first media and a second reflection signal corresponding to an index of refraction of said second media; and if said received reflection signal meets or exceeds said threshold value, a determination is made that said first media is in contact with said reflective/refractive interface, and wherein if said received reflection signal is less than said threshold value, a determination is made that said second media is in contact with said reflective/refractive interface.

3. The sensor of claim 2, wherein said first media comprises a liquid and said second media comprises a gas.

4. The sensor of claim 3, wherein said first media comprises water and said second media comprises air.

5. The sensor of claim 2, wherein said first media comprises a liquid and said second media comprises an air/gas mixture.

6. The sensor of claim 1, further comprising:

an optical fiber positioned between said light source and said reflective/refractive interface to direct the optical signal to the interface.

7. The sensor of claim 1, further comprising:

an optical waveguide positioned between said light source and said reflective/refractive interface to direct the optical signal to the interface.

8. The sensor of claim 1, wherein said reflective/refractive interface comprises a dome made of a material that allows light to pass therethrough.

9. The sensor of claim 1, wherein said reflective/refractive interface comprises a bent portion of an optical fiber having a bend enabling leakage of light traveling through the optical fiber at the location of the bend, such that when the bent portion is contacting the liquid media, light traveling through the optical fiber refracts into the liquid media.

10. The sensor of claim 1, wherein said light source comprises a laser.

11. A method for sensing the presence of media in contact with the sensor, comprising:

emitting an optical signal from a light source;

detecting a reflection of said optical signal using a light sensitive receiver, said light sensitive receiver generating a reflection signal corresponding to an index of refraction of said media;

positioning a reflective/refractive interface between said light source and said media; and receiving said reflection signal and comparing said reflection signal with a predetermined threshold value;

wherein if said received reflection signal meets or exceeds said threshold value, a determination is made that a first media is in contact with said reflective/refractive interface, and wherein if said received reflection signal is less than said threshold value, a determination is made that said first media is not in contact with said reflective/refractive interface; and incorporating the sensor in a supercativational vehicle to sense a distance between said supercavitational vessel and a cavity wall formed by operation of said supercavitational vessel.

12. The method of claim 11, said sensor sensing the presence of said first or a second media, said first and second media having differing indices of refraction, further comprising:

generating, by said light sensitive receiver, a first reflection signal corresponding to an index of refraction of said first media and a second reflection signal corresponding to an index of refraction of said second media;

determining that said first media is in contact with said reflective/refractive interface if said received reflection signal meets or exceeds said threshold value; and determining that said second media is in contact with said reflective/refractive interface if said received reflection signal is less than said threshold value.

13. The method of claim 12, wherein said first media comprises a liquid and said second media comprises a gas.

14. The method of claim 13, wherein said first media comprises water and said second media comprises air.

15. The method of claim 12, wherein said first media comprises a liquid and said second media comprises an air/gas mixture.

16. The method of claim 11, further comprising:

positioning an optical fiber between said light source and said reflective/refractive interface to direct the optical signal to the interface.

17. The method of claim 11, further comprising:

positioning an optical waveguide between said light source and said reflective/refractive interface to direct the optical signal to the interface.

18. The method of claim 11, wherein said reflective/refractive interface comprises a dome made of a material that allows light to pass therethrough.

19. The method of claim 11, wherein said reflective/refractive interface comprises a bent portion of an optical fiber having a bend enabling leakage of light traveling through the optical fiber at the location of the bend, such that when the bent portion is contacting the liquid media, light traveling through the optical fiber refracts into the liquid media.

20. The method of claim 1, wherein said light source comprises a laser.

* * * * *